US 6,242,476 B1
United States Patent
Mita et al.

(10) Patent No.: US 6,242,476 B1
(45) Date of Patent: Jun. 5, 2001

(54) LEUKOTRIENE $A_4$ HYDROLASE INHIBITORS

(75) Inventors: Shiro Mita; Masato Horiuchi; Masakazu Ban; Ken-ichi Fujimura; Hiroshi Suhara, all of Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/381,256

(22) PCT Filed: Mar. 25, 1998

(86) PCT No.: PCT/JP98/01300

§ 371 Date: Sep. 17, 1999

§ 102(e) Date: Sep. 17, 1999

(87) PCT Pub. No.: WO98/43954

PCT Pub. Date: Oct. 8, 1998

(30) Foreign Application Priority Data

Mar. 27, 1997 (JP) .................................... 9-074780

(51) Int. Cl.[7] ................. A61K 31/401; A61K 31/4015; A61P 29/00; C07D 207/12; C07D 207/16
(52) U.S. Cl. ......................... 514/423; 514/424; 514/428; 548/530; 548/533
(58) Field of Search .................... 514/423, 424, 514/428; 548/530, 533

(56) References Cited

U.S. PATENT DOCUMENTS 4,316,906  2/1982  Ondetti et al. ................. 424/274

FOREIGN PATENT DOCUMENTS 55-15457  2/1980  (JP) .

OTHER PUBLICATIONS

Elizabeth M. Smith et al., Synthesis and Pharmacological Activity of Angiotensin Converting Enzyme Inhibitors: N–(Mercaptoacyl)–4–Substituted–(S)–Prolines, *J. Med. Chem.*, (1988), 31, 875–885.

Lloyd B. Klickstein et al., "Lipoxygenation of Arachidonic Acid as a Source of Polymorphonuclear Leukocyte Chemotactic Factors in Synovial Fluid and Tissue in Rheumatoid Arthritis and Spondyloarthritis", *J. Clin. Invest.*, (1980), 66, 1166–1170.

S.D. Brain et al., "Leukotriene $B_4$–like Material in Scale of Psoriatic Skin Lesions", *Br. J. Pharmacol.*, (1984), 83 313–317.

Pichas Sharon and William F. Stenson, "Enhanced Synthesis of Leukotriene $B_4$ by Colonic Mucosa in Inflammatory Bowel Disease", *Gastroenterology*, (1984), 86, 453–460.

S.A. Rae et al., "Leukotriene $B_4$, An Inflammatory Mediator in Gout", *Lancet*, (1982), 2, 1122–1123.

Richard Lawrence and Tania Sorell, "Eicosapentaenoic Acid in Cystic Fibrosis: Evidence of a pathogenetic Role for Leukotriene $B_4$", *Lancet*, (1993), 342, 465–469.

*Primary Examiner*—Jane C. Oswecki
(74) *Attorney, Agent, or Firm*—Frishauf, Holtz, Goodman, Langer & Chick, P.C.

(57) ABSTRACT

The present invention relates to leukotriene $A_4$ hydrolase inhibitors containing compounds represented by the formula [I] or salts thereof as active ingredients,

[I]

wherein $R^1$ represents hydrogen, alkyl, phenylalkyl, alkanoyl or benzoyl; $R^2$ and $R^3$ each represent hydrogen or alkyl; $R^4$ represents hydroxyl, alkoxy, phenylalkoxy, amino, alkylamino or phenylalkylamino; $R^5$ represents phenylalkyl or naphthylalkyl; "Z" represents sulfur or oxygen; "A" represents alkylene; and "n" represents 0, 1 or 2; providing that the phenyl ring in $R^1$ can be substituted by alkyl, alkoxy or halogen, and that the phenyl ring or the naphthyl ring in $R^5$ can be substituted by alkyl, cycloalkyl, alkoxy, alkylthio or halogen.

14 Claims, No Drawings

LEUKOTRIENE A⁴ HYDROLASE INHIBITORS

This application is a 371 of PCT/JP98/01300 filed Mar. 25, 1998.

TECHNICAL FIELD

The present invention relates to leukotriene $A_4$ hydrolase inhibitors containing mercaptoacylproline derivatives as active ingredients and particularly provides useful drugs as therapeutic agents for inflammatory diseases such as rheumatic diseases.

BACKGROUND ART

Leukotriene $A_4$ (hereinafter abbreviated as $LTA_4$) hydrolase, which is one of epoxide hydrolases, is a metal-containing enzyme which requires zinc in its active center.

$LTA_4$ hydrolase plays a catalyst-like role on biochemical conversion from $LTA_4$ into leukotriene $B_4$ (hereinafter abbreviated as $LTB_4$), which is a strong pro-inflammatory substance.

$LTB_4$ is an arachidonic acid metabolite which is produced in 5-lipoxygenase pathway, is biosynthesized in various cells including mast cell, neutrophil, monocyte, macrophage, etc., and plays a role as an important mediator in inflammation. $LTB_4$ induces chemotaxis, aggregation and degranulation of leukocyte and accumulation of polymorphonuclear leukocyte, and accelerates blood-vessel permeability and edema formation. For this reason, it was reported that particularly high level of $LTB_4$ is detected at lesion sites in inflammatory diseases such as rheumatic diseases (J. Clin. Invest., 66, 1166–1170 (1980)), psoriasis (Br. J. Pharmacol., 83, 313–317 (1984)), inflammatory bowel diseases (Gastroenterology, 86, 453–460 (1984)) and gout (Lancet, 2, 1122–1124 (1982)), and in sputum in cystic fibrosis (Lancet, 342, 465–469 (1993)).

Accordingly, compounds which inhibit $LTA_4$ hydrolase are expected to prevent production of $LTB_4$ and exhibit therapeutic effects on inflammatory diseases such as rheumatic diseases.

Mercaptoacylproline derivatives, which are active ingredients in the present invention, are reported in U.S. Pat. No. 4,316,906 and J. Med. Chem., 31, 875–885 (1988) as antihypertensive agents having inhibitory effects on ACE. However, there is no report about $LTA_4$ hydrolase inhibition effects of compounds having a substituent in 4th-position of proline skeleton of these mercaptoacylproline derivatives. Compounds having a (lower cycloalkylphenyl)alkyl group in 4th-position of proline skeleton are novel compounds which are not described in literature.

As mentioned above, the mercaptoacylproline derivatives are known to have the inhibitory effects on ACE and to be useful as the antihypertensive agents. However, it is a very interesting subject to find new medical use of these compounds.

The present inventors studied in order to find new medical use of the known mercaptoacylproline derivatives and mercaptoacylproline derivatives synthesized newly. As a result, these compounds were found to exhibit excellent inhibitory activities on $LTA_4$ hydrolase.

DISCLOSURE OF THE INVENTION

The present invention relates to $LTA_4$ hydrolase inhibitors containing compounds represented by the following general formula [I] or salts thereof (hereinafter referred to as the present compounds) as active ingredients and novel compounds represented by the following general formula [II] or salts thereof.

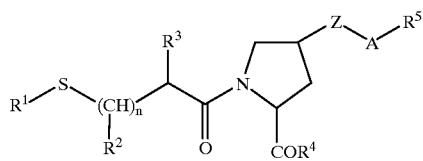

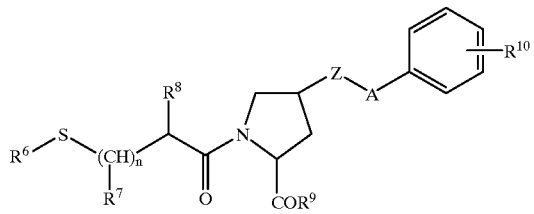

The groups defined above will be described in more detail. The lower alkyl means straight or branched lower alkyl having 1 to 6 carbon atoms such as methyl, ethyl, propyl, butyl, hexyl or isobutyl. The lower alkanoyl means straight or branched alkanoyl having 2 to 6 carbon atoms such as acetyl, propionyl, butyryl, hexanoyl, isobutyryl or pivaloyl. The lower alkoxy means straight or branched lower alkoxy having 1 to 6 carbon atoms such as methoxy, ethoxy, propoxy, butoxy or hexyloxy. The lower cycloalkyl means cyclic lower cycloalkyl having 3 to 8 carbon atoms such as cyclopropyl, cyclobutyl, cyclopentyl, cyclohexyl, cycloheptyl or cyclooctyl. The halogens atom means fluorine, chlorine, bromine and iodine. The lower alkylene means straight or branched lower alkylene having 1 to 6 carbon atoms such as methylene, ethylene, propylene or butylene.

Preferred examples of the above-mentioned compounds include the followings.

Compounds of the above general formula [I] wherein $R^1$ represents a hydrogen atom, a lower alkanoyl group or a benzoyl group, particularly preferably a hydrogen atom, and salts thereof.

Compounds of the above general formula [I] wherein $R^2$ represents a hydrogen atom or a lower alkyl group, particularly preferably a hydrogen atom, and salts thereof.

Compounds of the above general formula [I] wherein $R^3$ represents a hydrogen atom or a lower alkyl group, particularly preferably a methyl group, and salts thereof.

Compounds of the above general formula [I] wherein $R^4$ represents a hydrogen group or a lower alkyl group, particularly preferably a hydroxyl group, and salts thereof.

Compounds of the above general formula [I] wherein $R^5$ represents a phenyl group or a naphthyl group which can be substituted by a lower alkyl group, a lower cycloalkyl group, a lower alkoxy group or a lower alkylthio group, more preferably a phenyl group which can be substituted by a lower alkyl group or a lower cycloalkyl group, particularly preferably a phenyl group which can be substituted by an isopropyl group, a t-butyl group or a cyclohexyl group, and salt thereof.

Compounds of the above general formula [I] wherein "Z" represents a sulfur atom or an oxygen atom, particularly preferably a sulfur atom, and salt thereof.

Compounds of the above general formula [I] wherein "A" represents a lower alkylene group, particularly preferably a methylene group, and salts thereof.

Compounds of the above general formula [I] wherein "n" represents 0, 1 or 2, particularly preferably 1, and salts thereof.

Specific examples of particularly preferred compounds are (4S)-4-(4-isopropylbenzylthio)-1-[(2S)-3-mercapto-2-methylpropionyl]-L-proline, (4S)-4-(4-t-butylbenzylthio)-1-[(2S)-3-mercapto-2-methylpropionyl]-L-proline and (4S)-4-(4-cyclohexylbenzylthio-1-[(2S)-3-mercapto-2-methylpropionyl]-L-proline, which are represented by the following formulae [III], [IV] and [V], respectively, and salts thereof.

[III]

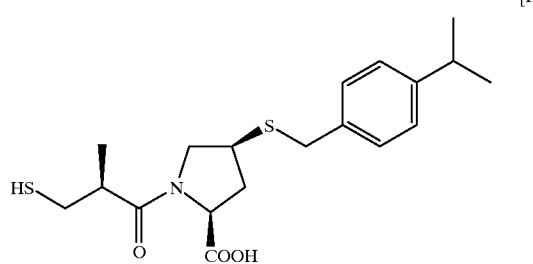

[IV]

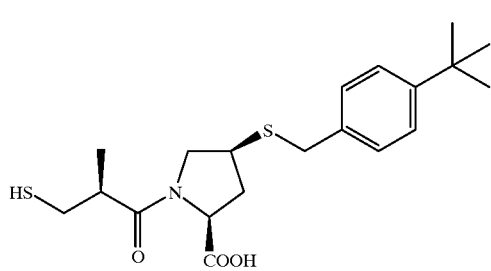

[V]

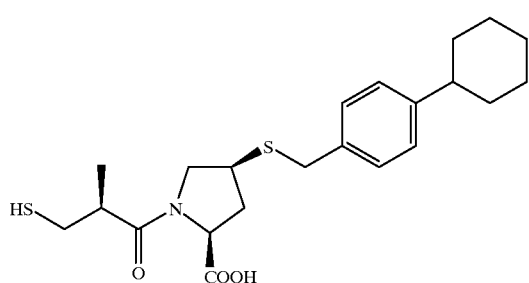

Among the novel compounds represented by the above general formula [II], the following compounds are exemplified as preferred compounds.

Compounds of the above general formula [II] wherein $R^6$ represents a hydrogen atom, a lower alkanoyl group or a benzoyl group, particularly preferably a hydrogen atom, and salts thereof.

Compounds of the above general formula [II] wherein $R^7$ represents a hydrogen atom or a lower alkyl group, particularly preferably a hydrogen atom, and salts thereof.

Compounds of the above general formula [II] wherein $R^8$ represents a hydrogen atom or a lower alkyl group, particularly preferably a methyl group, and salts thereof.

Compounds of the above general formula [II] wherein $R^9$ represents a hydroxyl group or a lower alkoxy group, particularly preferably a hydroxyl group, and salts thereof.

Compounds of the above general formula [II] wherein $R^{10}$ represents a lower cycloalkyl group, particularly preferably a cyclohexyl group, and salts thereof.

Compounds of the above general formula [II] wherein "Z" represents a sulfur atom or an oxygen atom, particularly preferably a sulfur atom, and salts thereof.

Compounds of the above general formula [II] wherein "A" represents a lower alkylene group, particularly preferably a methylene group, and salts thereof.

Compounds of the above general formula [II] wherein "n" represents 0, 1 or 2, particularly preferably 1, and salts thereof.

Specific examples of particularly preferred compounds are (4S)-4-(4-cyclohexylbenzylthio)-1-[(2S)-3-mercapto-2-methylpropionyl]-L-proline, which is represented by the following formula [V], and salts thereof.

[V]

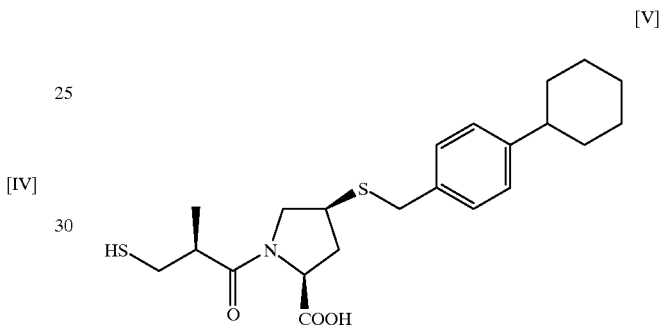

The above-mentioned salts can be any pharmaceutically acceptable salts. Examples thereof are hydrochlorides, sulfates, phosphates, lactates, maleates, fumarates, oxalates, methanesulfonates, para-topluenesulfonates, etc. In addition, diastereo isomers and optical isomers are present in the above-mentioned compounds, and all of them are included in the present invention. Furthermore, the above-mentioned compounds can be in the form of solvate, for example, hydrates, adducts with ethanol, etc.

In order to examine the utility of the mercaptoacylproline derivatives represented by the general formula [I] (hereinafter referred to as the present compound), studies were made on effects of the present compounds on $LTA_4$ hydrolase. The details will be shown in the pharmacological test described hereinafter. As the result of studies of the present compounds using $LTA_4$ as a substrate and measuring an amount of $LTA_4$ formed by an enzymatic reaction as an indication, the present compounds exhibited high inhibitory activities on $LTA_4$ hydrolase. Accordingly, the present compounds are expected to be useful for treatment of various diseases in which $LTA_4$ participates, particularly inflammatory diseases such as rheumatic diseases, psoriasis, inflammatory bowel diseases, gout and cystic fibrosis.

The results of the pharmacological test are those regarding only compounds wherein $R^1$ represents a hydrogen atom and $R^4$ represents a hydroxyl group, so-called an active compounds, among the compounds represented by the general formula [I]. However, these compounds, of course, can be administered in the form of prodrugs. Accordingly, it is a matter of course that compounds wherein $R^1$ is a group widely used as a protective group of a mercapto group, that is, a lower alkyl group, a phenyl-lower alkyl group, a lower alkanoyl group or a benzoyl group are also included in the present invention. In addition, a technique for converting a carboxyl group into ester or amide to form prodrugs is also widely used. Compounds wherein $R^4$ represents a lower alkoxy group, a phenyl-lower alkoxy group, an amino group, a lower alkylamino group or a phenyl-lower alkylamino group are also, of course, included in the present invention.

The present compound can be administered orally or parenterally. Examples of dosage forms are tablets, capsules, granules, powders, injections, etc. The present compound can be formulated into preparations by the conventional methods. For example, oral preparations such as tablets, capsules, granules and powders can be produced by adding optionally diluents such as lactose, crystalline cellulose, starch and vegetable oil; lubricants such as magnesium stearate and talc; binders such as hydroxypropylcellulose and polyvinyl pyrrolidone; disintegrator such as calcium carboxymethylcellulose or low-substituted hydroxypropylmethylcellulose; coating agent such as hydroxypropylmethylcellulose, macrogol or silicone resin; or gelatin film forming agent.

The dosage of the present compound can be selected suitably according to the symptom, age, dosage form and the like. In case of the oral preparation, the present compound can be administered once to several times per day with a daily dose of 0.1 to 5000 mg, preferably 1 to 1000 mg.

BEST MODE FOR CARRYING OUT THE INVENTION

Examples of preparations and results of pharmacological test of the present invention are shown below. These examples do not limit the scope of the invention, but are intended to make the invention more clearly understandable.

Preparation of Compounds

REFERENCE EXAMPLE 1

(4S)-4-(4-cyclohexylbenzylthio)-L-proline (reference compound No. 1)

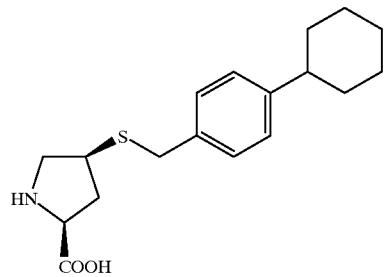

To (4S)-4-mercapto-L-proline hydrochloride (300 mg) is added 2 N sodium hydroxide (1.6 ml) aqueous solution, and the mixture is stirred at 0° C. A solution of 4-cyclohexylbenzyl chloride (340 mg) in a mixed solvent of ethanol (5 ml)/chloroform (1 ml) is added thereto, and the mixture is stirred at room temperature overnight. The reaction mixture is concentrated under reduced pressure, and deposited crystals are filtered off. The crystals are washed with water, ethanol and diethyl ether successively to give 470 mg (91%) of the titled compound.

mp 208.9–210.3° C.

EXAMPLE 1

1-[(2S)-3-Benzoylthio-2-methylpropionyl]-(4S)-4-(4-cyclohexylbenzylthio)-L-proline (compound No. 1)

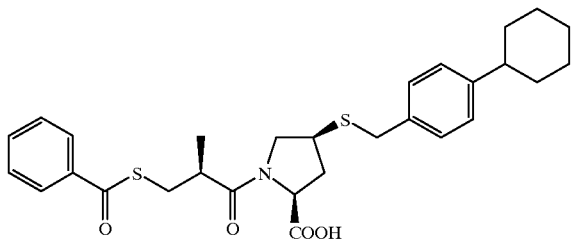

Dimethylformamide (4.5 ml) is added to (4S)-4-(4-hexylbenzylthio)-L-proline (430 mg), and the mixture is cooled to 0° C. To the mixture are added successively triethylamine (0.21 ml) and 4-nitrophenyl (2S)-3-(benzoylthio)-2-methylpropionate, and the obtained mixture is stirred at room temperature overnight. To the reaction mixture is added 10% citric acid, and the whole is extracted with ethyl acetate. The organic layer is washed with water and a saturated sodium chloride aqueous solution successively and dried over sodium sulfate. The residue obtained by concentration under reduced pressure is purified by silica gel column chromatography to give 580 mg (81%) of the titled compound as an amorphous substance.

$[\alpha]_D^{20}$ –73.4° (c=0.5, methanol)

IR (film, cm$^{-1}$) 2924, 1744, 1659, 1447, 1207, 915, 755, 689

EXAMPLE 2

(4S)-4-(4-cyclohexybenzylthio)-1-[(2S)-3-mercapto-2-methylpropionyl]-L-proline (compound No. 2)

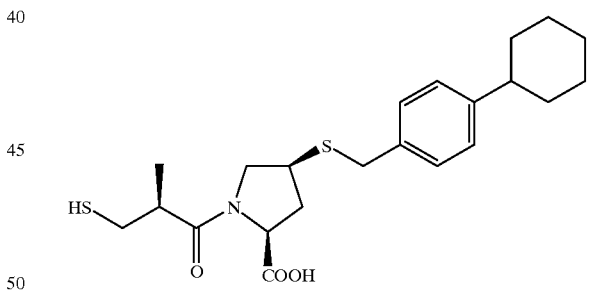

Under a nitrogen atmosphere, 28% aqueous ammonia (9 ml) is added to 1-[(2S)-3-benzoylthio-2-methylpropionyl]-(4S)-4-(4-cyclohexylbenzylthio)-L-proline (500 mg), and the mixture is stirred at room temperature for one hour. Ethyl acetate is added to the reaction mixture, and the whole is extracted with water. The aqueous layer is cooled to 0° C., 6 N hydrochloric acid is added thereto to adjust pH to 2, and the whole is extracted with ethyl acetate. The organic layer is washed with a saturated sodium chloride aqueous solution and dried over magnesium sulfate. The residue obtained by concentration under reduced pressure is purified by silica gel column chromatography to give 340 mg (87%) of the titled compound as an amorphous substance.

$[\alpha]_D^{20}$ –50.4° (c=0.5, methanol)

IR (film, cm$^{-1}$) 2924, 1736, 1641, 1612, 1463, 1446, 756

(4S)-4-Mercapto-L-proline hydrochloride and 4-nitrophenyl (2S)-3-(benzoylthio)-2-methylpropionate, which were used as raw materials in the above-mentioned Preparation of Compounds, are described in J. Org. Chem., 46, 4182–4187 (1981) and Japanese Laid-open Patent Publication 301840/1996, respectively.

Pharmacological Test

Izumi et al. had reported a method of measuring $LTA_4$ hydrolase activity by measuring an amount of $LTB_4$ produced by an enzymatic reaction using $LTA_4$ as a substrate (Biochem. Biophys. Res. Commun., 135, 139–145 (1986)). Effects of the present compounds on $LTA_4$ hydrolase were examined according to the method described in the literature.

Experimental Method

An enzyme preparation used in this pharmacological test was prepared by extracting from guinea pig lung without purification according to the method of Izumi et al. (Biochem. Biophys. Res. Commun., 135, 139–145 (1986)) and the method of Evans et al. (Biochem. Biophys. Acta, 840, 43–50 (1985)). The experimental method is as follows:

Lungs were excised from a Hartley guinea pig (body weight: 330 g). The lungs were homogenized in phosphoric acid buffer (50 mM, pH 7.4, containing 1 mM ethylenediaminetetraacetic acid (EDTA) and 1 mM dithiothreitol (DTT) having weight three times that of the lungs under ice-cooling. The homogenate was centrifuged at low speed (800×g) for 20 minutes, centrifuged at high speed (10,000× g) for 20 minutes and ultracentrifuged (100,000×g) for 60 minutes to give a supernatant. The supernatant was brought to 40% saturation by adding a saturated aqueous ammonium sulfate solution (pH 7.0–7.2, containing 1 mM DTT) dropwise under ice-cooling and centrifuged at high speed (10, 000×g) for 20 minutes. The resulting supernatant was brought to 70% saturation by adding a saturated aqueous ammonium sulfate solution (pH 7.0–7.2, containing 1 mM DTT) dropwise and centrifuged at high speed (10,000×g) for 20 minutes. The obtained pellet was dissolved in 2 ml of Tris-acetic acid buffer (20 mM, pH 7.8, containing 1 mM DTT) and dialyzed in 2 liters of the solution to give the enzyme preparation.

$LTA_4$ used, which is the substrate, was prepared by hydrolyzing $LTA_4$ methyl ester and dissolved in ethanol.

In order to examine effects of the test compounds on the enzyme preparation, reactions were performed under the following condition using mixed solutions consisting of the composition shown in Table 1.

TABLE 1

| HEPES buffer | 50 mM, pH 7.8 |
| --- | --- |
| Enzyme preparation | 0.4–0.6 mg protein |
| $LTA_4$ | 63 $\mu$M |
| DTT aqueous solution | 3 mM |
| Test compounds | $10^{-8}$–$10^{-3}$ M |

The above-mentioned solution (50 $\mu$l) was incubated at 37° C. for one minute. To the reaction mixture was added 100 $\mu$l of a mixed liquid of acetonitrile-ethanol-acetic acid (150:50:3, volume ratio) under ice-cooling. The mixture was allowed to stand at −20° C. for 30 minutes and centrifuged at high speed (10,000×g) for five minutes to give a supernatant. An amount of $LTB_4$ produced in the supernatant was measured by high-speed liquid chromatography.

The degree of the inhibitory effect of each test compound on $LTA_4$ hydrolase is expressed by the inhibition rate calculated by the following equation.

$$\text{Inhibition rate } (\%) = \frac{A - B}{A} \times 100$$

A: amount of $LTB_4$ formed in the absence of the test compound

B: amount of $LTB_4$ formed in the presence of the test compound

Results

Experimental results obtained by using the following compounds as representative examples of the test compound are shown in Table 2.

Compound a: 1-[(2S)-3-mercapto-2-methylpropionyl]-(4S)-4-(2-methylbenzylthio)-L-proline Compound b: (4S)-4-(4-isopropylbenzylthio)-1-[(2S)-3-mercapto-2-methylpropionyl]-L-proline Compound c: (4S)-4-(4-isopropylphenyethylthio)-1-[(2S)-3-mercapto-2-methylpropionyl]-L-proline Compound d: (4R)-4-(4-isopropylbenzylthio)-1-[(2S)-3-mercapto-2-methylpropionyl]-L-proline Compound e: (4R)-4-(4-isopropylbenzyloxy)-1-[(2S)-3-mercapto-2-methylpropionyl]-L-proline Compound f: (4S)-4-(4-butylbenzylthio)-1-[(2S)-3-mercapto-2-methylpropionyl]-L-proline Compound g: 1-[(2S)-3-mercapto-2-methylpropionyl]-(4S)-4-[4-(methylthio)benzylthio]-L-proline Compound h: (4S)-4-(4-cyclohexylbenzylthio)-1-[(2S)-3-mercapto-2-methylpropionyl]-L-proline The results are represented in concentration of the compounds required to inhibit $LTA_4$ hydrolase activity by 50%, i.e., $IC_{50}$.

TABLE 2

| | $IC_{50}$ (M) |
| --- | --- |
| Compound a | $8.4 \times 10^{-7}$ |
| Compound b | $5.2 \times 10^{-8}$ |
| Compound c | $7.9 \times 10^{-7}$ |
| Compound d | $2.9 \times 10^{-7}$ |
| Compound e | $8.0 \times 10^{-7}$ |
| Compound f | $3.1 \times 10^{-8}$ |
| Compound g | $1.2 \times 10^{-7}$ |
| Compound h | $3.4 \times 10^{-8}$ |

As shown in Table 2, the present compounds were found to inhibit the $LTA_4$ hydrolase activity remarkably at the low concentrations.

Since the above-mentioned pharmacological test shows that the present compounds have the excellent inhibitory effects on $LTA_4$ hydrolase, the compounds are expected to be, in particular, therapeutic agents for inflammatory diseases such as rheumatic diseases, psoriasis, inflammatory intestinal diseases, gout and cystic fibrosis, in which $LTB_4$ is concerned.

Industrial Applicability

The present invention relates to leukotriene $A_4$ hydrolase inhibitors containing mercaptoacylproline derivatives as active ingredients and particularly provides therapeutic agents for inflammatory diseases such as rheumatic diseases, psoriasis, inflammatory intestinal diseases, gout and cystic fibrosis, in which $LTB_4$ is concerned.

What is claimed is:

1. A method of treating a patient having an inflammatory disease comprising administering an effective leukotriene $A_4$ hydrolase inhibiting amount of a compound of the formula I or a pharmaceutically acceptable salt thereof,

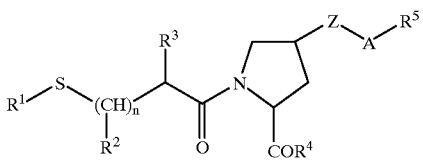

I wherein $R^1$ represents a hydrogen atom, a lower alkyl group, a phenyl-lower alkyl group, a lower alkanoyl group or a benzoyl group, and each phenyl ring of the phenyl-lower alkyl group and the benzoyl group can be substituted by a lower alkyl group, a lower alkoxy group or a halogen atom;

$R^2$ and $R^3$ each represent a hydrogen atom or a lower alkyl group;

$R^4$ represents a hydroxyl group, a lower alkoxy group, a phenyl-lower alkoxy group, an amino group, a lower alkylamino group or a phenyl-lower alkylamino group;

$R^5$ represents a phenyl group or a naphthyl group, and the phenyl group and the naphthyl group can be substituted by a lower alkyl group, a lower cycloalkyl group, a lower alkoxy group, a lower alkylthio group or a halogen atom;

"Z" represents a sulfur atom or an oxygen atom;

"A" represents a lower alkylene group; and

"n" represents 0, 1 or 2.

2. The method of claim 1, wherein in said compound of the formula I or a pharmaceutically acceptable salt thereof, $R^1$ represents a hydrogen atom, a lower alkanoyl group or a benzoyl group;

$R^2$ and $R^3$ each represent a hydrogen atom or a lower alkyl group;

$R^4$ represents a hydroxyl group or a lower alkoxy group;

$R^5$ represents a phenyl group or a naphthyl group, and the phenyl group can be substituted by a lower alkyl group, a lower cycloalkyl group, a lower alkoxy group or a lower alkylthio group;

"Z" represents a sulfur atom or an oxygen atom;

"A" represents a lower alkylene group; and

"n" represents 1.

3. The method of claim 1, wherein said compound of the formula I is selected from the group consisting of (4S)-4-(4-isopropylbenzylthio)-1-[(2S)-3-mercapto-2-methylpropionyl]-L-proline, (4S)-4-(4-butylbenzylthio)-1-[(2S)-3-mercapto-2-methylpropionyl]-L-proline, (4S)-4-(4-cyclohexylbenzylthio)-1-[(2S)-3-mercapto-2-methylpropionyl]-L-proline and pharmaceutically acceptable salts of said compounds.

4. A method of treating a patient having a rheumatic disease comprising administering an effective leukotriene $A_4$ hydrolase inhibiting amount of a compound of the formula I or a pharmaceutically acceptable salt thereof,

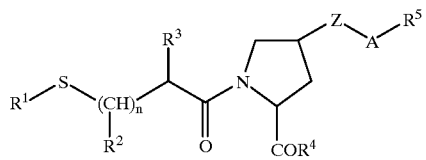

I wherein $R^1$ represents a hydrogen atom, a lower alkyl group, a phenyl-lower alkyl group, a lower alkanoyl group or a benzoyl group, and each phenyl ring of the phenyl-lower alkyl group and the benzoyl group can be substituted by a lower alkyl group, a lower alkoxy group or a halogen atom;

$R^2$ and $R^3$ each represent a hydrogen atom or a lower alkyl group;

$R^4$ represents a hydroxyl group, a lower alkoxy group, a phenyl-lower alkoxy group, an amino group, a lower alkylamino group or a phenyl-lower alkylamino group;

$R^5$ represents a phenyl group or a naphthyl group, and the phenyl group and the naphthyl group can be substituted by a lower alkyl group, a lower cycloalkyl group, a lower alkoxy group, a lower alkylthio group or a halogen atom;

"Z" represents a sulfur atom or an oxygen atom;

"A" represents a lower alkylene group; and

"n" represents 0, 1 or 2.

5. The method of claim 4, wherein in said compound of the formula I or a pharmaceutically acceptable salt thereof, $R^1$ represents a hydrogen atom, a lower alkanoyl group or a benzoyl group;

$R^2$ and $R^3$ each represent a hydrogen atom or a lower alkyl group;

$R^4$ represents a hydroxyl group or a lower alkoxy group;

$R^5$ represents a phenyl group or a naphthyl group, and the phenyl group can be substituted by a lower alkyl group, a lower cycloalkyl group, a lower alkoxy group or a lower alkylthio group;

"Z" represents a sulfur atom or an oxygen atom;

"A" represents a lower alkylene group; and

"n" represents 1.

6. The method of claim 4, wherein said compound of the formula I is selected from the group of (4S)-4-(4-isopropylbenzylthio)-1-[(2S)-3-mercapto-2-methylpropionyl]-L-proline, (4S)-4-(4-butylbenzylthio)-1-[(2S)-3-mercapto-2-methylpropionyl]-L-proline, (4S)-4-(4-cyclohexylbenzylthio)-1-[(2S)-3-mercapto-2-methylpropionyl]-L-proline and pharmaceutically acceptable salts of said compounds.

7. A pharmaceutically composition for treating inflammatory diseases comprising a carrier and a compound of the formula I or a pharmaceutically acceptable salt thereof,

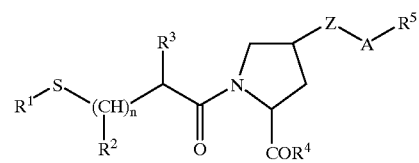

I wherein $R^1$ represents a hydrogen atom, a lower alkyl group, a phenyl-lower alkyl group, a lower alkanoyl group or a benzoyl group, and each phenyl ring of the phenyl-lower alkyl group and the benzoyl group can be substituted by a lower alkyl group, a lower alkoxy group or a halogen atom;

$R^2$ and $R^3$ each represent a hydrogen atom or a lower alkyl group;

$R^4$ represents a hydroxyl group, a lower alkoxy group, a phenyl-lower alkoxy group, an amino group, a lower alkylamino group or a phenyl-lower alkylamino group;

$R^5$ represents a phenyl group or a naphthyl group, and the phenyl group and the naphthyl group can be substituted by a lower alkyl group, a lower cycloalkyl group, a lower alkoxy group, a lower alkylthio group or a halogen atom;

"Z" represents a sulfur atom or an oxygen atom;

"A" represents a lower alkylene group; and

"n" represents 0, 1 or 2.

8. The pharmaceutical composition of claim 7 for treating a rheumatic disease.

9. The pharmaceutical composition of claim 8 wherein in said compound of the formula I or pharmaceutical acceptable salt thereof, $R^1$ represents a hydrogen atom, a lower alkanoyl group or a benzoyl group;

$R^2$ and $R^3$ each represent a hydrogen atom or a lower alkyl group;

$R^4$ represents a hydroxyl group or a lower alkoxy group;

$R^5$ represents a phenyl group or a naphthyl group, and the phenyl group can be substituted by a lower alkyl group, a lower cycloalkyl group, a lower alkoxy group or a lower alkylthio group;

"Z" represents a sulfur atom or an oxygen atom;

"A" represents a lower alkylene group; and

"n" represents 1.

10. The pharmaceutical composition of claim 9 wherein said compound is selected from the group consisting of (4S)-4-(4-isopropylbenzylthio)-1-[(2S)-3-mercapto-2-methylpropionyl]-L-proline and pharmaceutically acceptable salts thereof.

11. The pharmaceutical composition of claim 9 wherein said compound is selected from the group consisting of (4S)-4-(4-t-butylbenzylthio)-1-[(2S)-3-mercapto-2-methylpropionyl]-L-proline and pharmaceutically acceptable salts thereof.

12. The pharmaceutical composition of claim 10 wherein said compound is selected from the group consisting of (4S)-4-(4-cyclohexylbenzylthio)-1-[(2S)-3-mercapto-2-methylpropionyl]-L-proline and pharmaceutically acceptable salts thereof.

13. A compound represented by the following general formula [II] or a salt thereof,

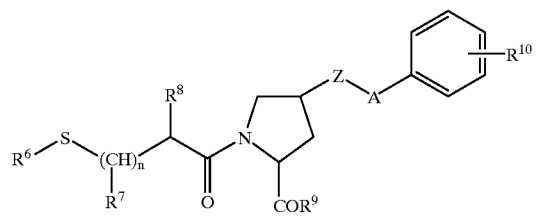

[II]

wherein $R^6$ represents a hydrogen atom, a lower alkyl group, a phenyl-lower alkyl group, a lower alkanoyl group or a benzoyl group, and each phenyl ring of the phenyl-lower alkyl group and the benzoyl group can be substituted by a lower alkyl group, a lower alkoxy group or a halogen atom;

$R^7$ and $R^8$ each represent a hydrogen atom or a lower alkyl group;

$R^9$ represents a hydroxyl group, a lower alkoxy group, a phenyl-lower alkoxy group, an amino group, a lower alkylamino group or a phenyl-lower alkylamino group;

$R^{10}$ represents a lower cycloalkyl group;

"Z" represents a sulfur atom or an oxygen atom;

"A" represents a lower alkylene group; and

"n" represents 0, 1 or 2.

14. The compound of claim 13 which is (4S)-4-(4-cyclohexylbenzylthio)-1-[(2S)-3-mercapto-2-methylpropionyl]-L-proline or a pharmaceutically acceptable salt thereof.

* * * * *